United States Patent
Flickinger et al.

(10) Patent No.: US 9,622,733 B2
(45) Date of Patent: Apr. 18, 2017

(54) IMPLANT DELIVERY SYSTEMS, DEVICES, AND METHODS

(71) Applicant: Meditech Spine, LLC, Atlanta, GA (US)

(72) Inventors: Eric Flickinger, Atlanta, GA (US); Jason J. Gromek, Cleveland, OH (US)

(73) Assignee: MEDITECH SPINE, LLC, Atlanta, GA (US)

( * ) Notice: Subject to any disclaimer, the term of this patent is extended or adjusted under 35 U.S.C. 154(b) by 322 days.

(21) Appl. No.: 14/277,476

(22) Filed: May 14, 2014

(65) Prior Publication Data

US 2014/0343559 A1  Nov. 20, 2014

Related U.S. Application Data

(60) Provisional application No. 61/823,462, filed on May 15, 2013.

(51) Int. Cl.
*A61B 17/02* (2006.01)
*A61F 2/46* (2006.01)
*A61F 2/30* (2006.01)

(52) U.S. Cl.
CPC .......... *A61B 17/025* (2013.01); *A61F 2/4611* (2013.01); *A61B 2017/0256* (2013.01); *A61F 2002/30331* (2013.01); *A61F 2002/30571* (2013.01); *A61F 2002/4627* (2013.01)

(58) Field of Classification Search
CPC .... A61B 17/88; A61B 17/025; A61B 17/0256
See application file for complete search history.

(56) References Cited

U.S. PATENT DOCUMENTS

| 5,431,658 | A | * | 7/1995 | Moskovich | A61B 17/025 606/90 |
| 7,615,079 | B2 | | 11/2009 | Flickinger et al. | |
| 7,935,053 | B2 | * | 5/2011 | Karpowicz | A61B 1/32 600/205 |
| 8,114,088 | B2 | * | 2/2012 | Miller | A61F 2/4465 606/90 |
| 8,137,284 | B2 | * | 3/2012 | Miles | A61B 1/32 600/554 |
| 2015/0105624 | A1 | * | 4/2015 | Martinelli | A61B 17/3423 600/204 |

OTHER PUBLICATIONS

Synthes Spine, "Luminary ALIF—Disc Preparation and Implant Insertion Instructions" Technique Guide, 2006, 25 pages.

* cited by examiner

*Primary Examiner* — Andrew Yang
(74) *Attorney, Agent, or Firm* — Kilpatrick Townsend & Stockton LLP

(57) ABSTRACT

Provided are modular implant delivery systems, devices and methods. In some embodiments, spinal implant delivery devices and methods are provided. An exemplary delivery device may include a head supported by a handle. The head may have an opening defining an insertion axis. The handle may have a handle axis that traverses the insertion axis. The head may also be configured to releasably couple one or more blades.

19 Claims, 12 Drawing Sheets

IMPLANT DELIVERY SYSTEMS, DEVICES, AND METHODS

CROSS-REFERENCES TO RELATED APPLICATIONS

The present application claims the benefit of U.S. Provisional Patent Application No. 61/823,462 filed May 15, 2013 and entitled "Implant Delivery System," the disclosure of which is incorporated in its entirety herein by reference.

FIELD OF THE INVENTION

Embodiments of the invention generally relate to spinal fusion surgery.

BACKGROUND OF THE INVENTION

The spinal column is a flexible column formed from a linear series of vertebral bones separated by intervertebral discs. These discs reduce friction between adjacent vertebrae and absorb compression forces applied to the spinal column. A vertebra includes an anterior body and a posterior arch that surrounds the spinal cord. Spinal nerves extend from each side of the spinal cord and exit the column at the vertebral foramen, which is formed by the posterior arch. Articular processes, including the superior articular process and the inferior articular process, are small flat projections on the surfaces of the arches.

There are four facet joints associated with each vertebrae, and these joints interlock with adjacent vertebrae. In this manner, facets on the opposing processes determine the range and direction of movement between adjacent vertebrae, hence the flexibility of the spinal column. The facet joints maintain spinal stability, protect the disc from excessive stress, and assist the discs in allowing motion and controlling shear forces. These joints are vulnerable to degenerative spinal disorders.

Degenerative disc disease is typically caused by a loss of disc space height, leading to a narrowing of the neural foramen and subsequent neural compression, and causing back and radicular pain. Instability of the posterior elements can lead to a condition known as spondylolisthesis, in which a vertebral body slips forward in relation to an adjacent vertebrae. This movement of the vertebral body narrows the foramen and results in painful pressure on the nerve roots.

Degenerative disc disease may be resolved through a spinal fusion procedure using an interbody implant (which is implanted between the bodies of two adjacent vertebrae). Such interbody implants may be formed from titanium, carbon fiber, allograft, or other suitable material including, but not limited to, biocompatible materials such as PEEK (Polyetheretherketone)™. Implantation of a substitute graft is designed to reestablish normal disc height, provide immediate stability to the motion segment, and provide a matrix for fusion. When the implant grows into the existing bone, the fusion becomes solid and movement is eliminated at that level. A fusion procedure may also involve the surgical implantation of hardware, such as plates, screws or cages.

In order to fuse and thereby stabilize the motion segment, the disc space must be prepared prior to insertion of the interbody device. Soft tissue, such as disc material and cartilage, and other such tissue is cleaned off the vertebral endplates so that intimate bony contact is obtained between the graft, implant and host tissue. The preparation of the disc space can be achieved with scrapers, curettes, rongeurs, drills, rasps and/or chisels. In preparing the disc space, it is important not to remove too much of the endplate in order to maintain structural integrity so that the interbody implant does not telescope into the vertebral body when normal axial loads are applied.

Posterior Lumbar Interbody Fusion (PLIF) is one surgical fusion technique used to treat degenerative lumbar disc disease. Proper distraction during a PLIF procedure must be achieved in order to gain compression of the implant. Proper distraction allows natural compression across the disc space via the annulus and other posterior elements. This compression delivered to the implant helps stabilize the implant, which avoids expulsion, and keeps the grafting material under stress, thus promoting faster fusion and bone healing.

Transforaminal Lumbar Interbody Fusion (TLIF), also referred to as an extended PLIF, was developed in response to problems associated with PLIF procedures. In the TLIF approach, the disc space is expanded by removing one entire facet joint, while a PLIF is usually performed on both sides of the facet, removing a portion of each of the joints. Removal of the entire facet joint improves visualization into the disc space, allowing removal of more disc material and insertion of a larger implant. Other procedures have been developed to provide anterior column support as well, including the Anterior Lumbar Interbody Fusion (ALIF) and extreme lateral interbody fusion techniques that access the vertebrae through the psoas muscle.

SUMMARY OF THE INVENTION

The terms "invention," "the invention," "this invention" and "the present invention" used in this patent are intended to refer broadly to all of the subject matter of this patent and the patent claims below. Statements containing these terms should not be understood to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the entire specification of this patent, all drawings and each claim.

Disclosed are systems and methods for controlled delivery of instruments for disc preparation and controlled insertion of implants into the prepared disc space. In some embodiments, disclosed is a device that may be used as both a distractor and as a guide for inserting implants, such as, but not limited to, spinal fusion implants. In some embodiments, the device is configured for use with additional instruments. The disclosed device may be used for PLIF, TLIF, ALIF, lateral, and cervical spine procedures, or any other desired procedure.

In some aspects, spinal implant delivery devices are provided. The implant delivery devices may include a handle and a head supported by the handle. The head may include an opening for receiving a spinal implant therethrough and defining a tool insertion axis. In some embodiments, the handle may have an elongate length defining a handle axis, and the handle axis may traverse or intersect with the tool insertion axis.

The head may further include a first pair of engagement features positioned on opposite sides of the opening. The first pair of engagement features may be configured to couple with one or more removable blades. In some embodiment, the first pair of engagement features may be configured to couple with corresponding engagement features of the one or more removable blades. In some embodiments, the head may further comprise a second pair of engagement features positioned on opposite sides of the opening. The second pair of engagement features may be configured to couple with one or more removable blades. In some embodiments, the second pair of engagement features may be configured to couple with corresponding engagement features of the one or more removable blades. Accordingly, in some embodiments, the first pair of engagement features and the second pair of engagement features may permit removable attachment of at least four removable blades to the head of the implant delivery device.

Optionally, the handle axis and the tool insertion axis may intersect at an angle between 90-110°. In some embodiments, the handle axis and the tool insertion axis are perpendicular to one another.

The opening of the head may be defined by an inner wall. The inner wall may be keyed or configured to fittingly engage a body of a received implant holder so as to restrict translational movement of the implant holder to movement along the tool insertion axis. The inner walls may guide the implant holder as the implant holder slides or rotates along the tool insertion axis to deliver a spinal implant.

The device may include an implant holder having a body with a rectangular cross-section. The inner wall of the opening may define a rectangular opening corresponding to the rectangular cross-section of the implant holder body.

Optionally, the inner walls of the opening may be threaded to couple with threads on a received implant holder. The device may further have an implant holder having a body with a circular cross-section. The inner wall of the opening may define a circular opening corresponding to the circular cross-section of the implant holder body. The threads of the opening may cooperate with the threads of the implant holder to couple a rotational motion of the implant holder about the tool insertion axis with a translational motion of the implant holder along the tool insertion axis.

In some embodiments, the implant holder may have a body with distance indicia along a length of the implant holder. The implant holder may cooperate with the head to identify a distance indicia corresponding to a position of the implant holder along the tool insertion axis.

In further aspects of the present invention, spinal implant delivery devices are provided. An elongate body may define a handle and have a handle axis. A head may be supported by the handle. The head may include an opening for receiving a spinal implant therethrough and defining a tool insertion axis. The tool insertion axis may traverse or intersect with the handle axis.

The head may further comprise a first pair of engagement features positioned on opposite sides of the opening. The engagement features may be configured to couple with corresponding engagement features of one or more removable distractor blades.

Also disclosed is a method for inserting a spinal implant to a deployment site within a patient. A spinal implant delivery device may be used which has a handle and a head with an opening supported by the handle. The method may include coupling a first disc distractor blade with a first engagement feature of the head of the spinal implant delivery device and coupling a second disc distractor blade with a second engagement feature of the head of the spinal implant delivery device. The second engagement feature may be on an opposite side of the opening from the first engagement feature. The spinal implant may be delivered through the opening of the head of the spinal implant delivery device. Then the spinal implant may be deployed from the spinal implant delivery device. After deployment, the spinal implant delivery device may be withdrawn from within patient. The method may further include removing the first disc distractor blade and the second disc distractor blade from the head of the spinal implant delivery device. The removed disc distractors may then be sterilized (e.g., autoclaved) or disposed of.

In some embodiments, methods may include coupling the spinal implant with a distal end of an implant holder and manipulating a proximal end of the implant holder to translate the spinal implant distally along a tool insertion axis. A distal end of the first distractor blade and a distal end of the second distractor blade may be separated by translating the spinal implant proximal to the distal ends of the first and second distractor blades.

Optionally, methods may further include coupling a first soft tissue distractor to the head of the spinal implant delivery device and coupling a second soft tissue distractor to the head of the spinal implant delivery device. The first and second disc distractor blades and the first and second soft tissue distractor blades may define a rectangular channel for receiving and deploying the spinal implant. The first and second soft tissue distractors may also be removed from the head of the spinal implant delivery device after deploying the spinal implant and withdrawing the spinal implant delivery device from within the patient. The soft tissue distractors may then be sterilized (e.g., autoclaved) or disposed of.

In some embodiments, the opening of the head may be defined by an inner wall. The methods disclosed above may further include sliding the implant holder through the opening of the head of the spinal implant delivery device and engaging a portion of the implant holder with inner wall such that translational movement of the implant holder is restricted to translational movement along the tool insertion axis.

Optionally, a portion of the implant holder may include threads and the inner wall may include corresponding threads. The methods may further include threading the threads of the implant holder with the threads of the inner wall. The threading of the corresponding threads may couple a rotation motion of the implant holder with a translational motion of the implant holder along the tool insertion axis.

BRIEF DESCRIPTION OF THE DRAWINGS

A full and enabling disclosure including the best mode of practicing the appended claims and directed to one of ordinary skill in the art is set forth more particularly in the remainder of the specification. The specification makes reference to the following appended figures, in which use of like reference numerals in different features is intended to illustrate like or analogous components.

DETAILED DESCRIPTION OF THE DRAWINGS

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1:
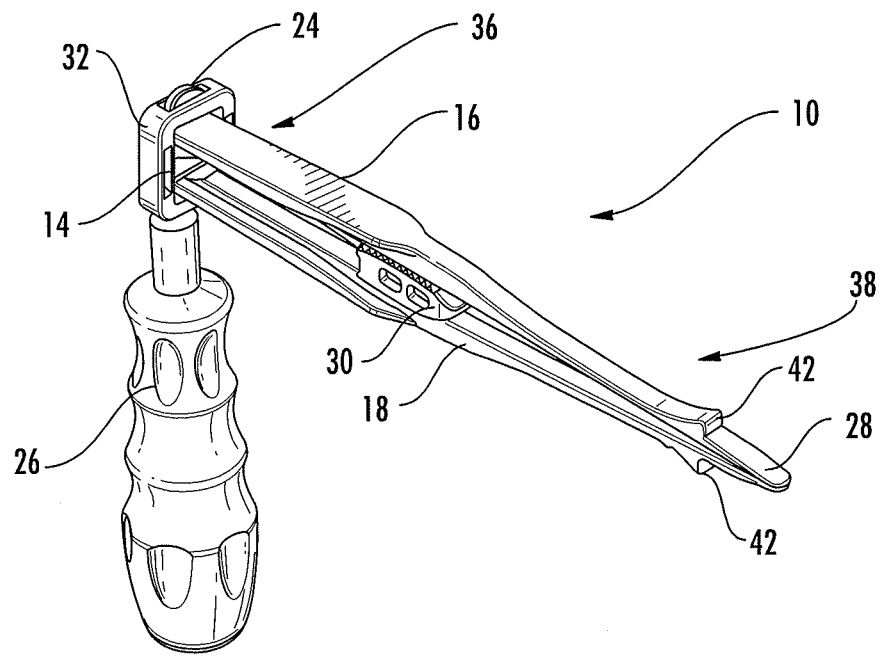
FIG. 1 is a side, top perspective view of a delivery device assembly according to one embodiment, assembled with two blades and shown with an implant positioned between the two blades.

Disclosed herein are systems, devices, and methods for facilitating the performance of a surgical procedure. In some non-limiting embodiments, the systems, devices, and methods facilitate spinal fusion procedures. FIGS. 1-11 illustrate a number of views of exemplary implant delivery device 10 in different configurations. As shown in FIG. 1, a device 10 may be provided to protect the medial neural structures and facilitate the controlled delivery of an insert (such as but not limited to insert 30) into the disc space. Insert 30 may be a spinal implant such as a spinal fusion implant.

Device 10 may include a handle 26 that supports a head 32. Handle 26 may have an elongate body defining a handle axis 27 (FIG. 6) along the elongate body. The handle 26 may be ergonomically configured for gripping by a hand of an operator. Head 32 may include an opening 34 (FIG. 8) and one or more engagement features positioned about the head opening 34. The opening 34 may be defined by an inner wall 33 (FIG. 3) of head 32. The opening 34 may be dimensioned to accommodate and receive various instruments therethrough. For example, nerve root retractors, soft tissue and muscle retractors, implant inserters, rongeurs, osteotomes, distractors, curettes and disc scrapers may be inserted and used through the opening 34. It should be understood that this list is exemplary and not intended to be exhaustive. The opening 34 may also define a tool insertion axis 35 (FIG. 6) and may be configured to receive a spinal implant 30 generally along the tool insertion axis 35. Preferably, tool insertion axis 35 intersects with handle axis 27 to form an angle between approximately 90°±60°. For example, in some embodiments the angle between tool insertion axis 35 and handle axis 27 may be 90-110°. Optionally, axis 35 and axis 27 may be perpendicular to one another. In some embodiments, handle 26 may couple with head 32 via a lockable hinge joint or a gear mechanism to allow for a range of angles between handle axis 27 and tool insertion axis 35. The hinge joint or gear mechanism may allow for adjustment of the angle between the tool insertion axis 35 and the handle axis 27 to a preferred angle (e.g., personal or for a particular procedure).

In some embodiments, having the handle 26 off axis relative 27 to the insertion axis 32 may keep the handle 26 out of view from the surgeon and thus keep the handle 26 from obstructing the surgeon's line of site. Further, the off-axis handle 26 may accommodate a more comfortable angle for surgeon use. Optionally, the handle 26 may be removeably coupled with head 32. If needed, the handle 26 may be removed and the head 32 may be anchored to a bed via a rigid arm.

While the opening 34 is illustrated with a generally rectangular cross-section when viewed along the tool insertion axis 35 (FIG. 8), opening 34 may have other configurations. As one non-limiting example, the opening 34 may have a circular cross-section when viewed along the tool insertion axis 35.

The one or more engagement features of exemplary head 32 illustrated in FIGS. 1-11 comprise a first set of slot apertures 12 positioned on opposites sides of opening 34 from one another and a second set of slot apertures 14 positioned on opposites sides of the opening 34 from one another. The first and second set of apertures 12, 14 may be configured for coupling with various instruments. For example, in some embodiments, the one or more engagement features 12, 14 may couple with tissue separator blades, retractor blades, distractor blades, dilators, or the like. Thus, in the illustrated embodiment 10, head 32 may releasably couple with at least four blades about opening 34. While generally discussed with two sets of engagement features 12, 14, it should be understood that any suitable number of engagement features may be used.

The first set of apertures 12 includes a top aperture positioned above opening 34 and distal from the handle 26 and a bottom aperture positioned below the opening 34 and proximal to the handle 26. The first set of apertures 12 may define openings along the inner wall 33 of head 34. The first set of apertures 12 may couple with one or more surgical instruments by receiving a corresponding engagement feature of the surgical instrument in a direction generally transverse to the tool insertion axis 35 (e.g., direction 74 or direction 76, FIG. 6). In some embodiments, a surgical instrument may be coupled with the head 32 by positioning a portion of the surgical instrument within opening 34 and then translating the instrument away from the insertion axis 35 to engage the top (e.g., direction 76) or the bottom aperture 12 (e.g., direction 74).

Figure 8:
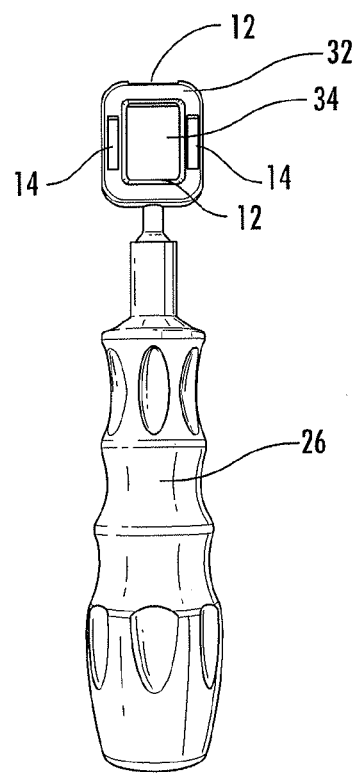
FIG. 8 is a rear view of the delivery device assembly of FIG. 1.
Figure 9:
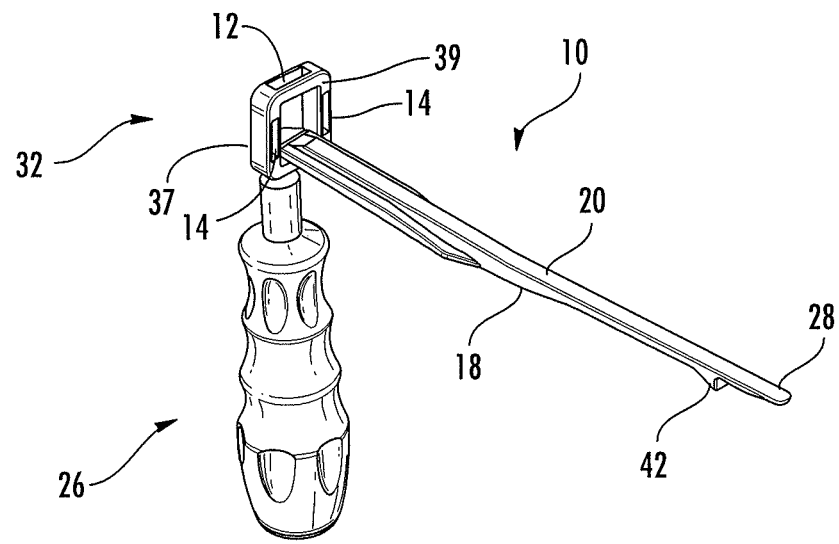
FIG. 9 is a side, top perspective view of the delivery device assembly of FIG. 1, assembled with a lower blade.
Figure 10:
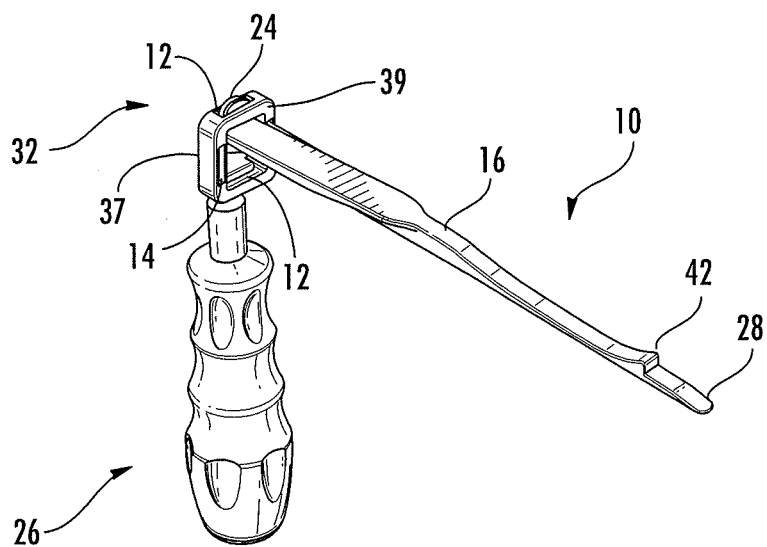
FIG. 10 is a side, top perspective view of the delivery device assembly of FIG. 1, assembled with an upper blade.
Figure 11:
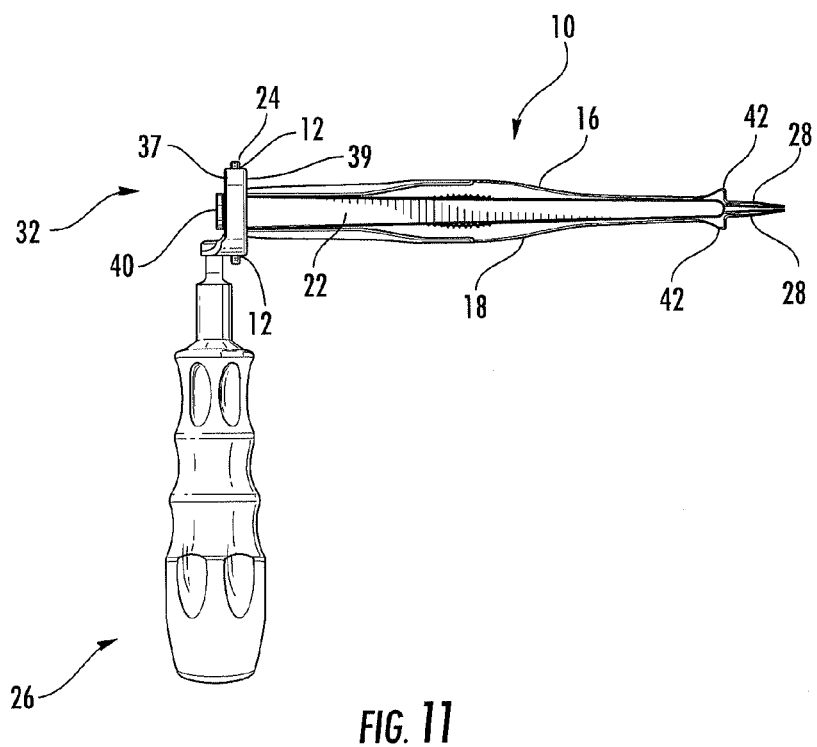
FIG. 11 is a side view of the delivery device assembly of FIG. 1, shown with two blades and two soft tissue retractors.

The second set of apertures 14 may include a left aperture positioned to the left of the opening 34 (when the opening 34 is viewed along the tool insertion axis 35 in a distal direction, FIG. 8) and a right aperture positioned to the right of opening 34. The second set of apertures 14 defines openings along a proximal face 37 and a distal face 39 of the head 32—distal face designates the side facing in the direction in which the device points when the device is in use, whereas proximal face designates the opposite side. The second set of apertures 14 may couple with one or more surgical instruments by receiving a portion of the surgical instrument body therethrough in a direction generally parallel to the tool insertion axis 35 (e.g., direction 71 or direction 72, FIG. 6). For example, in some embodiments, a distal tip of a surgical instrument may be inserted within an aperture 14 from a proximal side of the head 32. The surgical instrument may then be slid distally in direction 72 until the surgical instrument engages with the aperture 14. In some embodiments, the surgical instrument may fittingly engage aperture 14. Additionally or alternatively, the surgical instrument may include an abutment or projection that engages with the proximal face of head 32 to ensure that the surgical tool does not protrude too far in the distal direction 72.

Figure 2:
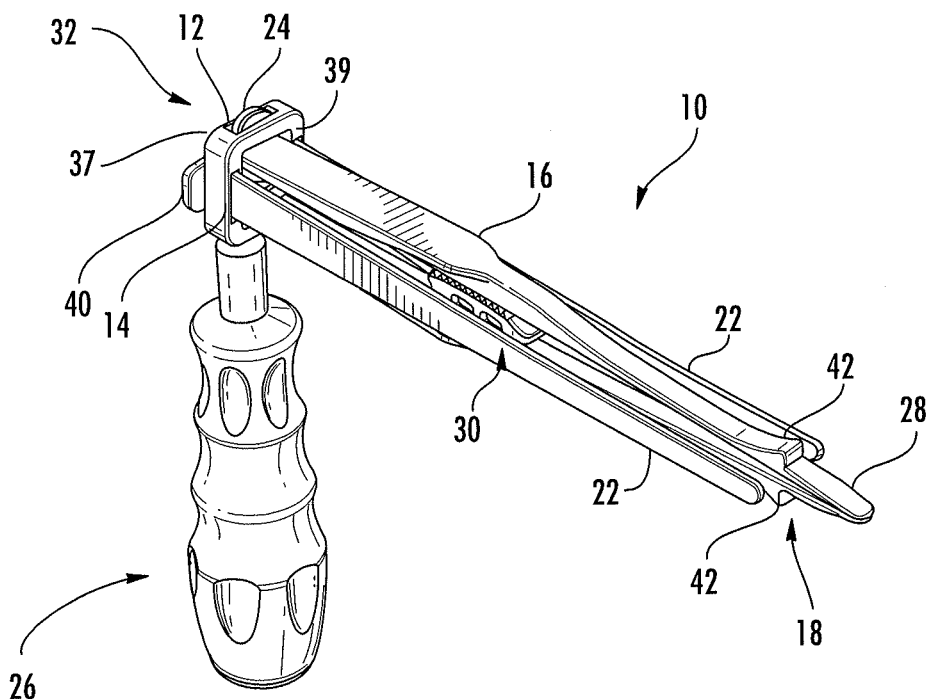
FIG. 2 is a side, top perspective view of the delivery device assembly of FIG. 1, assembled with two blades, two retractors, and shown with an implant positioned between the two blades.

While the device 10 is generally described and illustrated as having slot aperture engagement features 12, 14, it should be understood that other engagement features may be used. For example, some embodiments may use dovetail engagement features, snap fit engagement features, fastener engagement features, or the like. Further, in some embodiments, the engagement features may be configured to cooperate with corresponding engagement features or may be configured to secure a portion of a body of a received surgical instrument. Optionally, a surgical instrument may include engagement features that engage with a portion of the head 32. Accordingly, in some embodiments, head 32 may not require engagement features because surgical instruments may incorporate engagement features to secure themselves to head 32. FIG. 2 illustrates exemplary surgical instruments which may be coupled with head 32.

As shown in FIG. 1, one or more blades 16, 18 may releasably couple with head 32. Each blade 16, 18 may include an engagement feature corresponding to an engagement feature on the head 32. In the illustrated embodiment, each blade 16, 18 may include a blade abutment 24 that projects at an angle from the blade body and may be inserted into and abut apertures 12. The engagement of the blade abutments 24 with apertures 12 may retain the blades 16, 18 in a desired position relative to the head 32. As shown in FIG. 1, blades 16, 18 may be attached and configured so that they extend distally from the head 32 and taper toward each other from a proximal end 36 toward a distal end 38. The blades 16, 18 also include a tip 28, which may be tapered for easier insertion into the disc space. One or more of the blades 16, 18 may optionally include stops 42 (FIG. 4) at their distal ends 38 to prevent the blades 16, 18 from being inserted too far into the disc space.

In some embodiments, the blades 16, 18 are formed of metal or another sufficiently rigid structure to aid with the distraction. As shown in the Figures, the device 10 may be configured so that the distal end 36 of the blades 16, 18 has a relatively small profile to allow access into a collapsed disc space and allow for controlled distraction.

In some embodiments, blades 16 and 18 serve as distractors to maintain proper distraction within the disc space while the disc space is cleaned and prepared. Various instruments can be inserted through the opening 34 of the device 10 to push apart the tips 28 of the blades 16, 18 so the disc space can be cleaned and prepared. For example, a series of dilators or distractors may be pushed through the opening 34 to expand the blades 16, 18. Additionally, spinal implants (e.g., a spinal fusion implant) may be inserted through opening 34 of the device 10 and distally delivered to a deployment site within a patient.

Figure 3:
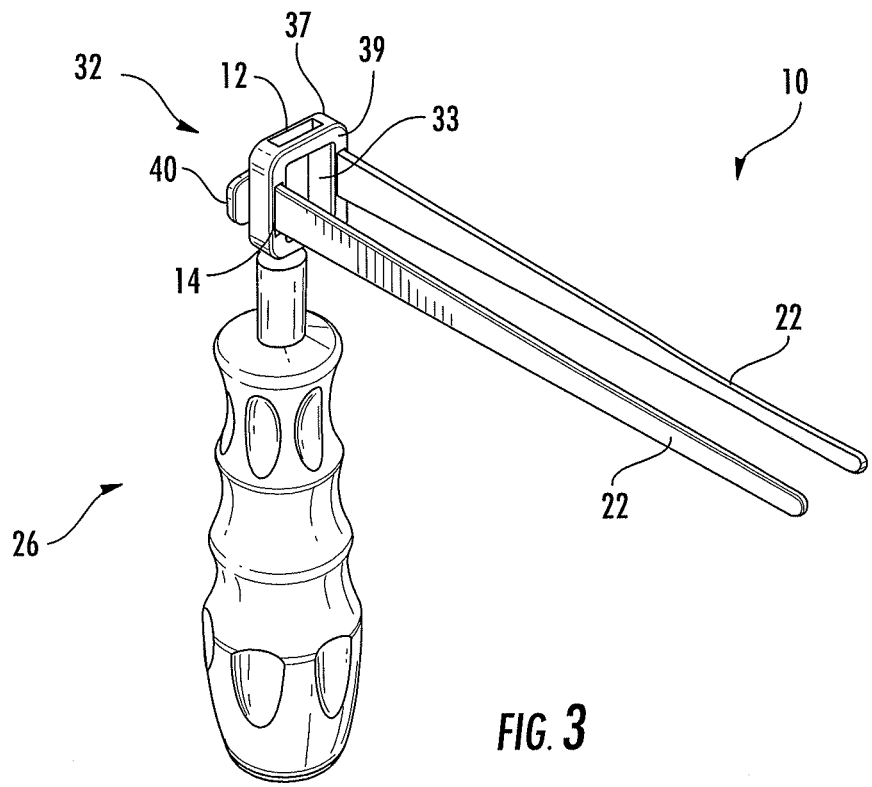
FIG. 3 is a side, top perspective view of the delivery device assembly of FIG. 1, shown with the two soft tissue retractors.
Figure 4:
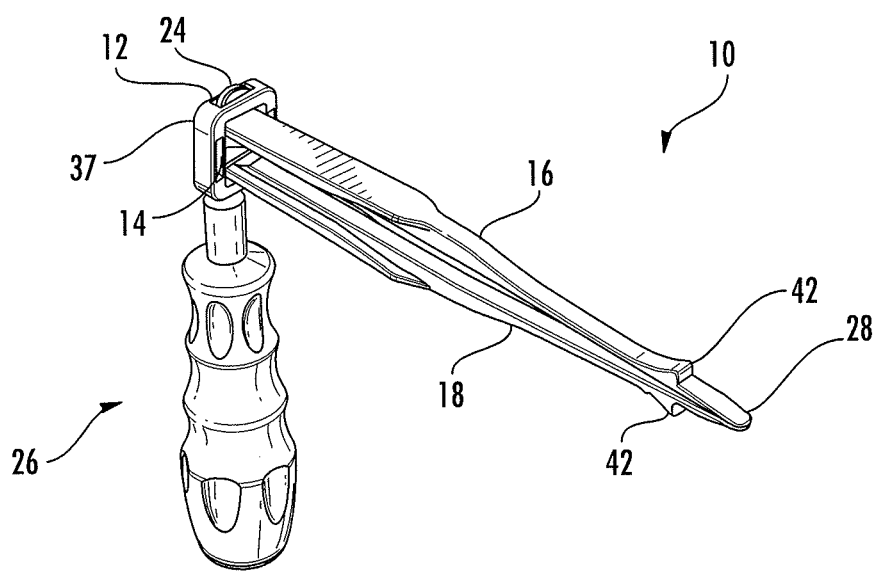
FIG. 4 is a side, top perspective view of the delivery device assembly of FIG. 1, shown with two blades.
Figure 5:
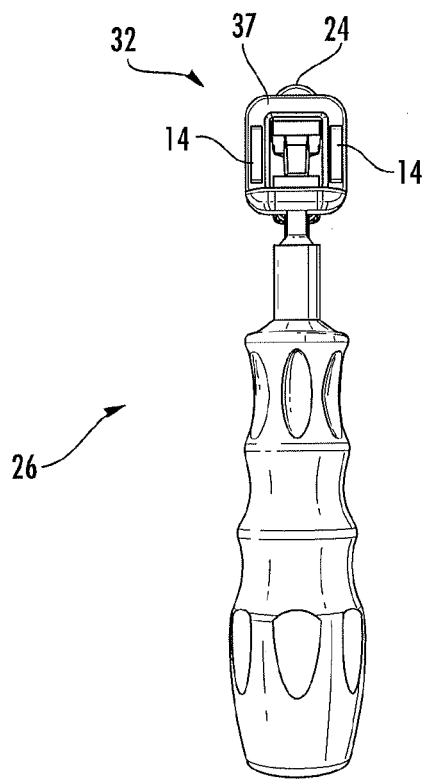
FIG. 5 is a rear view of the delivery device assembly of FIG. 1, shown with two blades.
Figure 6:
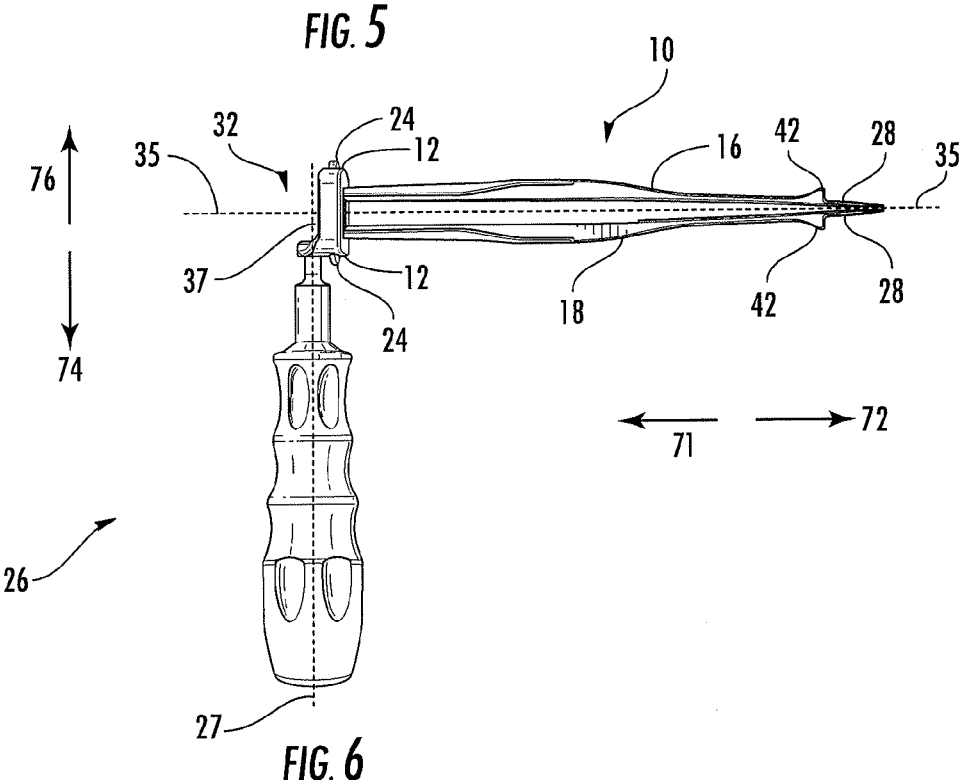
FIG. 6 is a side view of the delivery device assembly of FIG. 1, shown with two blades.
Figure 7:
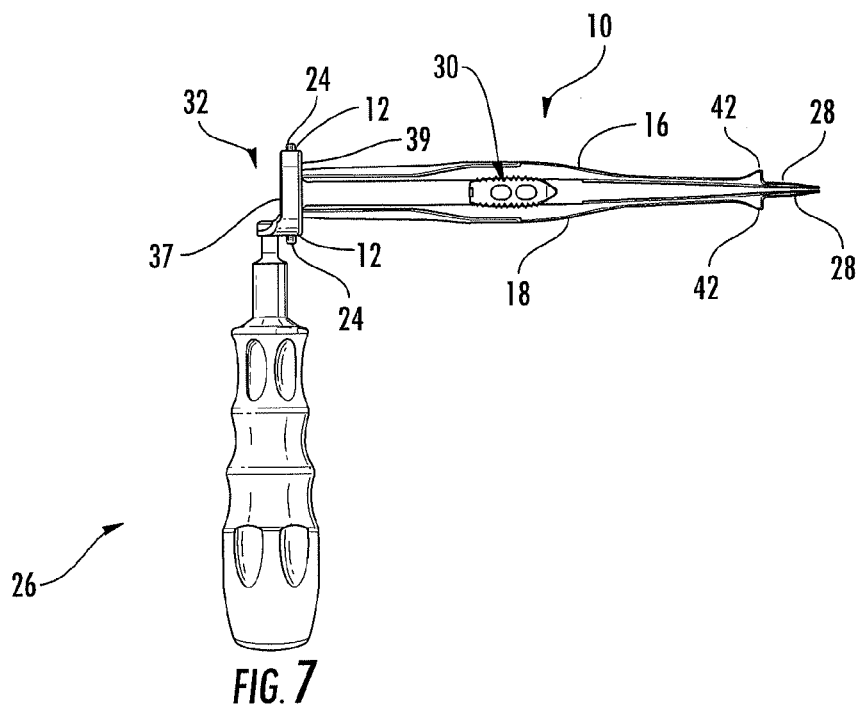
FIG. 7 is a side view of the delivery device assembly of FIG. 1, shown with two blades and an implant inserted between the two blades.

In some embodiments, one or more soft tissue distractors, such as soft tissue distractors/retractors 22, may be inserted through apertures 14, as shown in FIG. 3. If used, soft tissue distractors 22 may assist with moving the dura nerve sacks out of the way to reduce the risk of damage during the procedure. The soft tissue distractor 22 may include an abutment 40 that helps retain the distractor in position within the aperture 14 relative to the delivery device 10. In some cases, soft tissue distractor 22 could be a soft polymer and could be disposable. In other embodiments, soft tissue distractor 22 could be a relatively stiff metal that retracts the soft tissue (e.g., muscle or fascia) to keep it from encroaching and blocking the line of sight into the disc space.

The blades described above may be constructed of metal, plastic, or a combination thereof. Further, the blades may be rigid or flexible materials in construction. In some embodiments, where the surgical instruments are reusable, the removability of the surgical instruments from the device 10 may further simplify device and instrument sterilization (e.g., autoclave) after use. Further, being modular may also be beneficial for adding and removing different types of blades or different sized blades (width, length, etc.) that may be needed for different parts of the spine. The modularity may also allow for more functional pieces to be added when necessary. While the blades are illustrated as having one-piece construction that rigidly attach to head 32, other embodiments may use blades with hinge mechanisms for opening and closing the blades along the tool insertion axis 35.

Figure 12:
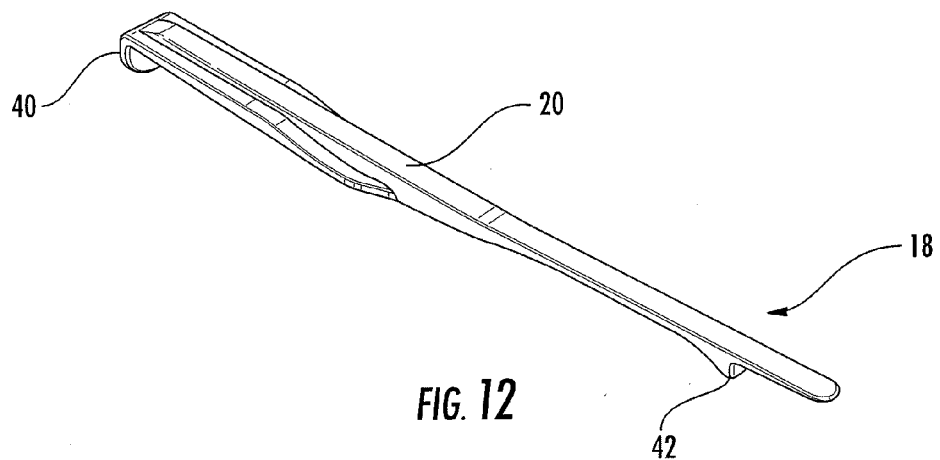
FIG. 12 is a top perspective view of a blade shown in isolation.
Figure 13:
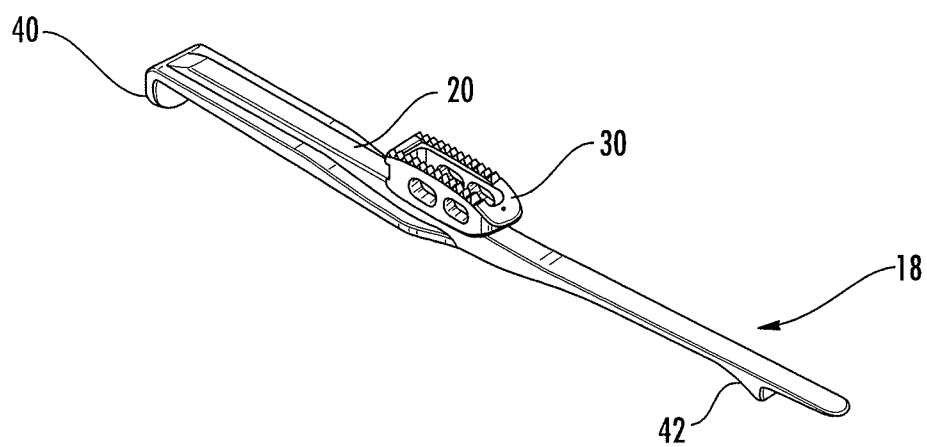
FIG. 13 is a side, top perspective view of a blade shown with an implant.

As shown in FIG. 12, the lower blade 18 may include an elevated rail 20, along which an implant (such as implant 30) can slide, as illustrated in FIG. 13, when under compression. The rail 20 may help guide the implant 30 along the insertion axis 35 and into the disc space. In some embodiments, the implant 30 can be configured with a ridge that corresponds to the rail 20. While illustrated with rail 20 located along a top surface of the lower blade 18, it should be understood that a guide rail may be located along the bottom surface of the top blade 16 or may be located along soft tissue distractors 22. In some embodiments, each of the blades may include guide rails that help guide the implant along the insertion axis 35.

As disclosed herein, the delivery device 10 may be configured as a modular tool that is universal in nature. For example, the delivery device 10 may be designed so that various blades (e.g., blades 16, 18, 22, or the like) can be secured into any of the apertures 12, 14 of the head 32 of the device 10. In this way, the apertures 12, 14 may be designed to accommodate various instruments. Moreover, the delivery device 10 may be used as a retractor as well as a distractor.

In addition, the delivery device 10 may be configured to be received within or otherwise cooperate with a tube system such as, but not limited to, the METRx™ system or any other minimally invasive tube. In some embodiments, the head 32 itself can be incorporated into existing tube systems to dock the instruments within a tube. In some embodiments, the instruments can be locked and/or rotatable within the tube.

Figure 14:
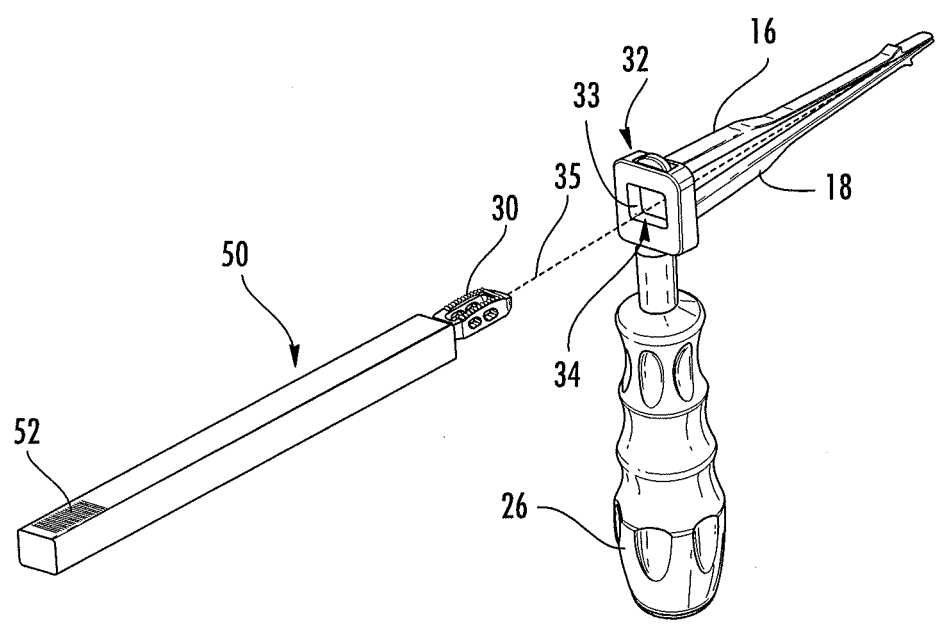
FIG. 14 illustrates a system with an implant holder coupled with an implant and the cooperation of the implant holder body with the inner walls of the head of a delivery device.

Further, in some embodiments, the device may include an implant holder 50 (FIG. 14). The implant holder 50 may couple with an implant (e.g., implant 30) and may facilitate distal delivery of the implant 30 along the tool insertion axis 35.

In some embodiments, the implant holder 50 may be an impacted type and the inner wall 33 of the head 32 may be keyed to slideably and fittingly engage a body of the implant holder 50. The engagement between the inner wall 33 of head 32 and implant holder 50 may restrict translational movement of the implant holder 50 to movement along the tool insertion axis 50. Further, when the opening and the implant holder have corresponding non-circular cross-sections, the engagement may restrict rotational movement of the implant holder 50 relative to head 32. Accordingly, with such an embodiment, inner walls 33 may guide the implant holder 50 and restrict rotation of the implant holder 50 and a coupled implant 30 as the implant holder 50 slides and/or is impacted along the tool insertion axis 35. The cooperation between inner walls 33 of head 32 and the body of the implant holder 50 may facilitate a controlled deployment of implant 30 along tool insertion axis 35 and into a deployment site within a patient.

Optionally, implant holder 50 may include indicia 52 on a portion of the implant holder 50 that provides a depth scale. Accordingly, as the implant holder 50 translates distally relative to the device 10, the head 32 (e.g., proximal 37 or distal end face 39) may identify an indicia 52 corresponding to a depth of the implant holder 50 and/or implant 30 relative to the head 32. This indicia 52 may provide additional information to an operator to facilitate the controlled delivery of a spinal implant.

Figure 15:
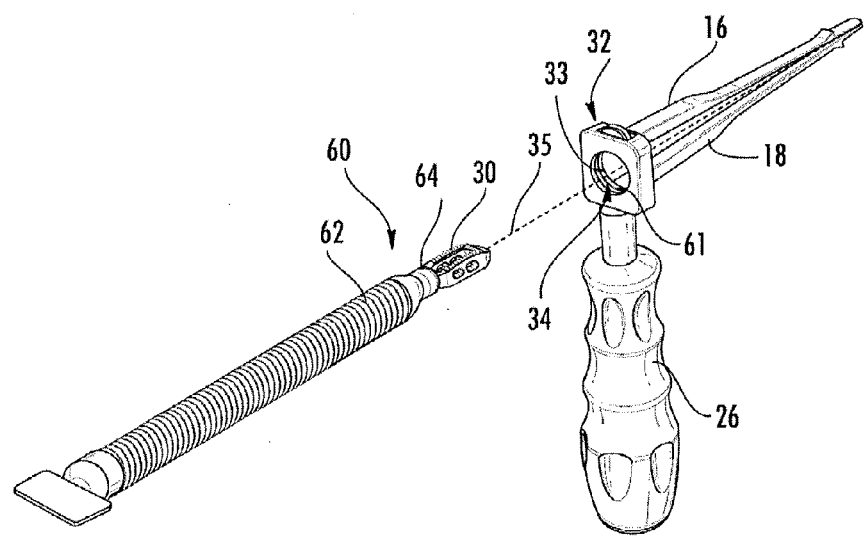
FIG. 15 illustrates another system with an implant holder coupled with an implant and the cooperation of the implant holder body with the inner walls of the head of a delivery device.

While the implant holder 50 is illustrated with a generally rectangular cross-section that corresponds to the configuration of the inner wall 33, other configurations are possible. For example, as described above, the inner wall 33 of head 32 may define a circular opening 34. The circular opening 34 may correspond to a circular cross-section of the implant holder body 60 (FIG. 15). The circular opening 34 may cooperate with implant holder 60 in a manner similar to that described above. Put another way, inner walls 33 of a circular opening 34 may restrict movement of implant holder 60 to translational movement along the insertion axis 35 to facilitate a controlled deployment of an implant 30 as the implant 30 is delivered distally (e.g., impacted) toward the deployment site.

Optionally, the inner wall 33 may also incorporate threading which cooperates with threads on the implant holder 60 (FIG. 15). In such an implementation, the threads 61 of the inner wall 33 cooperate with the threads 62 of the implant holder 60 to couple a rotational motion of the implant holder 60 about the tool insertion axis 35 with a translational motion of the implant holder 50 along the tool insertion axis 35. An operator may rotate (manually or electrically) a proximal end of implant holder 60 about the insertion axis 35. As the operator rotates implant holder 60, the implant holder 60 and a coupled implant 30 may translate distally (or proximally) in a controlled fashion and may obviate the need for impacting. Preferably, a distal tip 64 of the implant holder 60 may be configured to allow free rotation of the distal tip 64 about the implant holder axis so that a coupled implant (e.g., implant 30) does not rotate when the implant 30 is compressed between the blades 16, 18 and as the proximal portion of the implant holder 60 is rotated about the tool insertion axis 35. Advantageously, this configuration may further control the distal deployment of an implant 30.

Also, the threading 62 may also act as distance indicia, similar to indicia 52 illustrated in FIG. 15. Optionally, separate distance indicia may be provided on implant holder 60. Thus, as an operator rotates implant holder 60 within opening 34, the operator may observe the threading 62 or other distance indicia to determine precise depth information corresponding to a distal portion of the implant holder 60 and/or the implant 30 along insertion axis 35.

Figure 16:
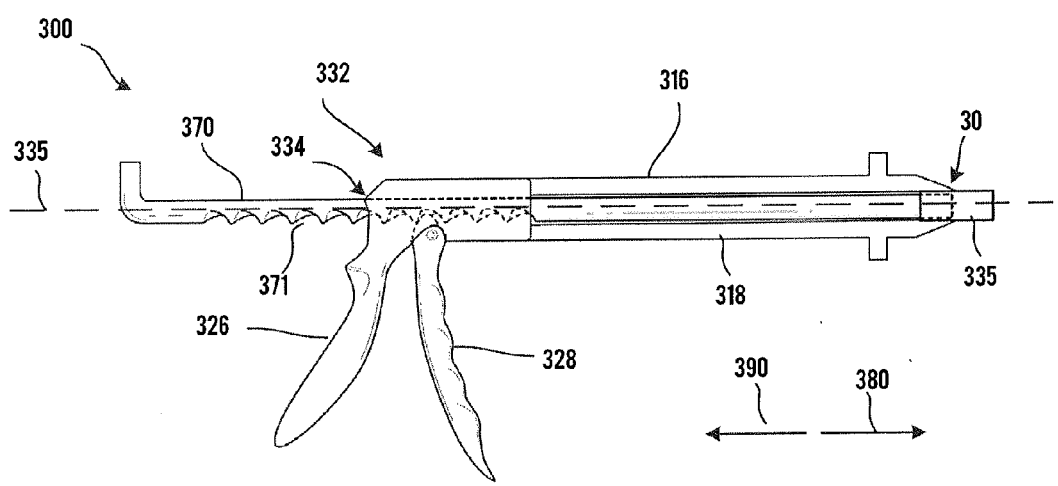
FIG. 16 illustrates yet another system for controlled delivery of an implant into a patient's disc space.
Figure 17:
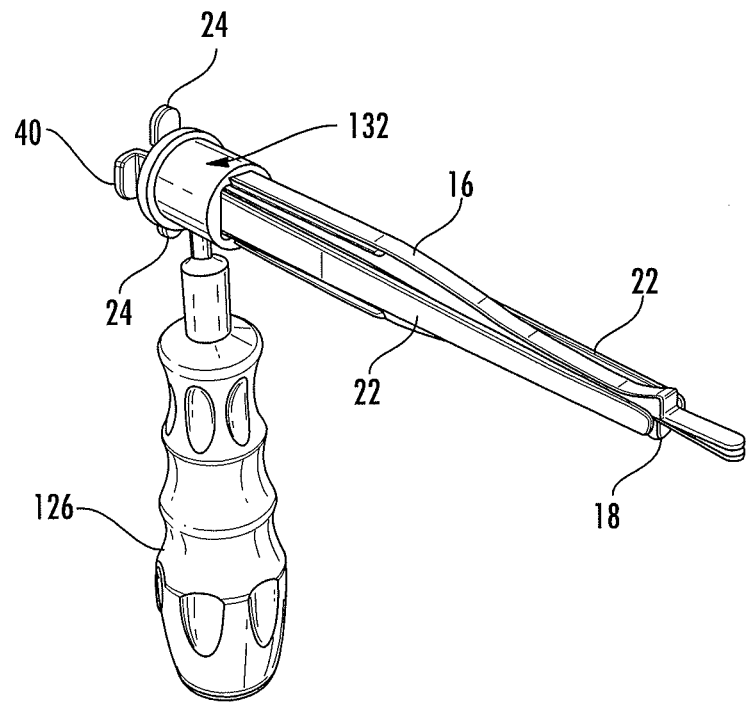
FIG. 17 is a side, top perspective view of another embodiment of an delivery device assembly, assembled with two blades and two soft tissue retractors.
Figure 18:
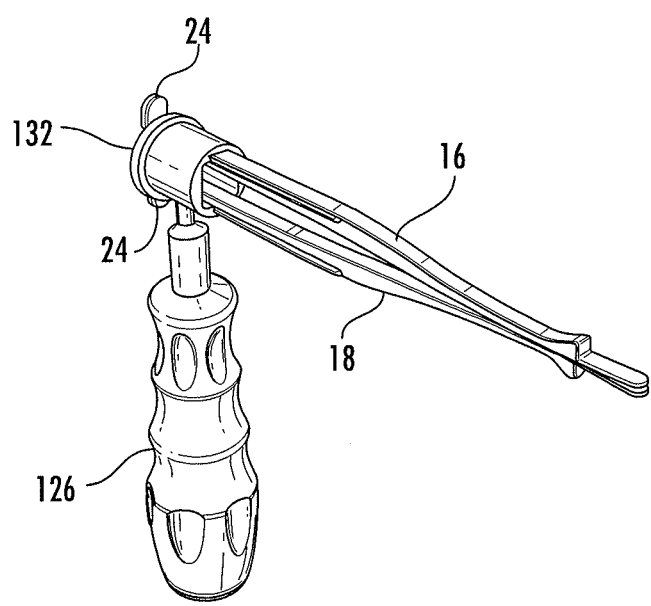
FIG. 18 is a side, top perspective view of the delivery device assembly of FIG. 17, shown without the two soft tissue retractors.

FIG. 16 illustrates an implant delivery device 300. Implant delivery device 300 includes a handle 326, a head 332 and a trigger 328. The head 332 may also include an opening 334 for receiving one or more tools therethrough. The head 332 may also releasably couple to one or more distractor blades similar to the embodiments discussed above. Head 332 is illustrated as releasably coupled with a top disc distractor blade 316 and a bottom disc distractor blade 318, and may releasably couple with soft tissue distractor blades (e.g., distractor blades 22).

The opening 334 may receive an implant 30 therethrough along the insertion axis 335 defined by the opening 334. An elongate shaft 370 may also be inserted along the opening 334. The shaft 370 may have grooves 371 along a first side of the shaft 370 and groove-free side opposite the first side. Optionally, the grooves 371 of the shaft 370 may cooperate with trigger 328 when engaged therewith such that actuation of the trigger 328 urges shaft 370 in the distal direction 380 along insertion axis 335. Optionally, the shaft 370 may releasably couple with implant 30 and act as a plunger to push implant 30 along insertion axis 335 to provide controlled delivery of the implant 30 into the disc space.

Such an embodiment may facilitate controlled distal delivery of an implant 30 along the insertion axis 335. To engage the grooves 371 of shaft 370 with the trigger 328, the shaft 370 may be positioned within the opening 334 of head 332 with the grooves 317 engaging with trigger 328 (as illustrated in FIG. 16). To disengage the grooves 371 of the shaft 370, the shaft 370 may be rotated within the opening 334 so that the grooves 371 are positioned away from the trigger 328. The groove-free side 372 of shaft 370 may be rotated to contact trigger 328 but may not cooperate with trigger 328 to urge shaft 370 in the distal direction 380 when trigger 328 is actuated. When disengaged, shaft 370 may be freely retracted in the proximal direction 390 along insertion axis 335 and may also be pushed (e.g., via impaction or the like) in the distal direction 380.

FIGS. 17-20 illustrate other embodiments of a device 100 configured for use with various tube systems. There are several tube dilation systems on the market which are used to distract and dilate soft tissue and provide an opening to the disc space. In essence this is a working channel with illumination either from the surgeon headlight or additional light pipettes added to the tubes. The exemplary device 100 may slide inside and nest with the tube so that the tools may function with an existing tube device. Further, the device 100 may be anchored on the tube and then operate in the same way as it would on its own except the tube may act as the soft tissue retractor.

Figure 19:
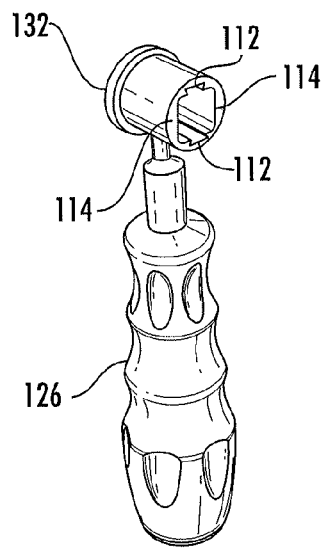
FIG. 19 is a side, top perspective view of the delivery device assembly of FIG. 17, shown without the two soft tissue retractors and without the two blades.
Figure 20:
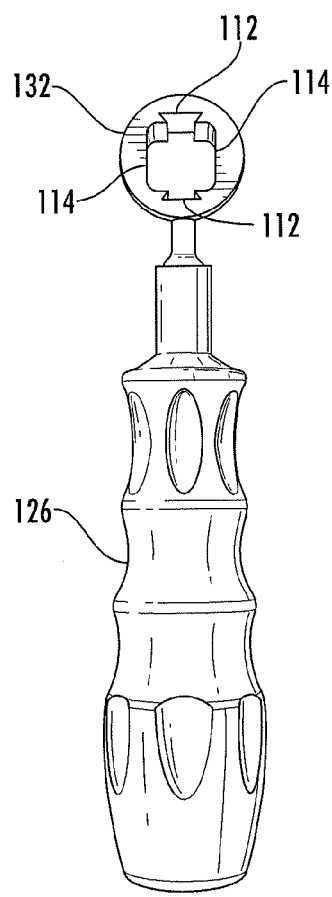
FIG. 20 is a rear perspective view of the delivery device assembly of FIG. 17.

The embodiment of FIGS. 17-20 is similar to the embodiments described above, except the head 132 may be dimensioned and otherwise configured to drop inside a tube, such as but not limited to a minimally invasive tube, to dock the device assembly 100 within the tubular system. The head 132 may also be configured with engagement features to receive blades and/or soft tissue distractors (e.g., blades 16, 18, 22) as discussed above. In some embodiments, the head 132 includes one or more dovetail engagement features 112 or guide channels 114 for receiving the blades (16, 18, 22) as shown in FIGS. 19-20. In some embodiments, an abutment 24, 40 of the blades and/or distractors (e.g., 16, 18, 22) abuts a proximal face of the head 132 and retains the blade and/or distractor from sliding forward in a distal direction.

Also disclosed is a device that delivers the implant via any suitable mechanical leverage tool. For example, handle 26 may have a first set of gears and a knob, while the head 32 may include a second set of gears that interface with the first set of gears. When the knob is turned, the first set of gears turn and engage the second set of gears, which in turn drive the implant into the disc space in a controlled fashion without the need for impacting, which in some cases can cause vibrations that can irritate the nerves. In this way, the delivery device can be configured to allow for insertion with a mallet or other suitable means of impacting or the insert can be mechanically delivered. Other alternatives for mechanical controlled delivery are also envisioned such as direct impaction of the delivery device or pneumatic delivery, etc.

Figure 21:
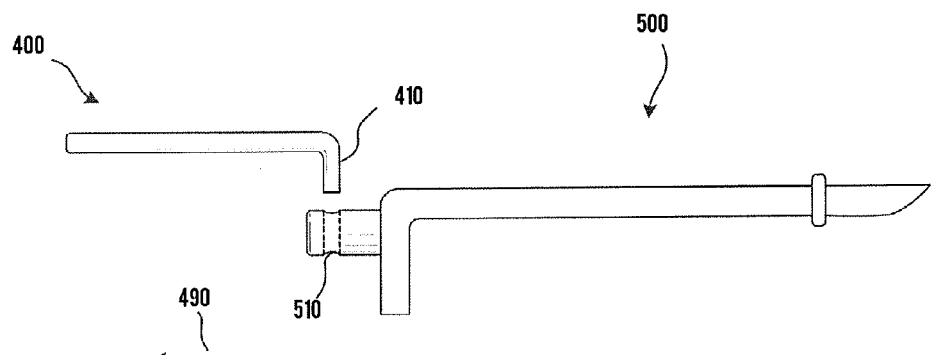
FIG. 21 illustrates exemplary cooperation between a blade removal tool and an exemplary blade according to some aspects of the invention.

In some embodiments, at least one of the blades, such as blade 16, 18, 22 or the like, may include a modified proximal portion that allows for engagement with another tool when it is under compression in the disc space to pull back and remove the blade from the disc space. FIG. 21 illustrates an exemplary removal tool 400 for removing a blade 500. Removal tool 400 may include an engagement feature 410 that cooperates with a portion of blade 500. Blade 500 may include a proximal engagement feature 510 that corresponds to engagement feature 410. Engagement feature 410 is illustrated as a hook that grabs engagement feature 510 (e.g., groove, loop, hole, or the like). When inserted in the disc space, engagement feature 410 may be hooked onto engagement feature 510. The removal tool 400 may then be withdrawn proximally 490 to facilitate the controlled removal of blade 500 from the disc space.

While engagement features 410, 510 are illustrated as hook and groove/loop type engagement features, other engagement features are possible. For example, FIGS. 22A-22D illustrate exemplary engagement features on the proximal portion of a blade 600.

Figure 22A:
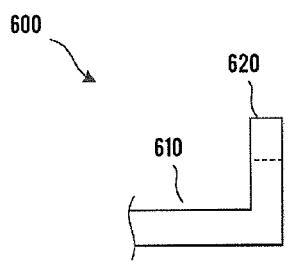
FIGS. 22A-22D illustrate exemplary blade engagement features for coupling a blade with a blade removal tool to facilitate controlled removal of the blade from a patient's disc space.

FIG. 22A illustrated a blade 600 with a blade body 610 and an abutment 620 extending from the blade body 610. The abutment 620 may extend substantially perpendicular from blade body 610. The abutment 620 may have a groove or slot 630 at a tip of the abutment 620 and along the distal face of abutment 620. A removal tool may couple with the groove or slot 630 to engage the blade 600 and to facilitate removal of blade 600 from the disc space.

Figure 22B:
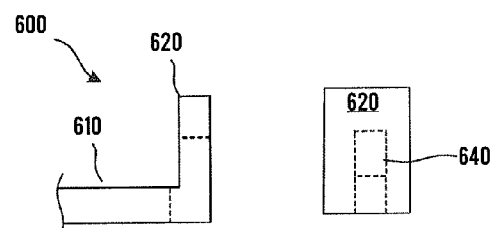

FIG. 22B illustrates another embodiment of blade 600 where a hole 640 may be positioned along a the joint between blade body 610 and blade abutment 620 and may extend from a distal face of abutment 620 to a proximal face of abutment 620.

Figure 22C:
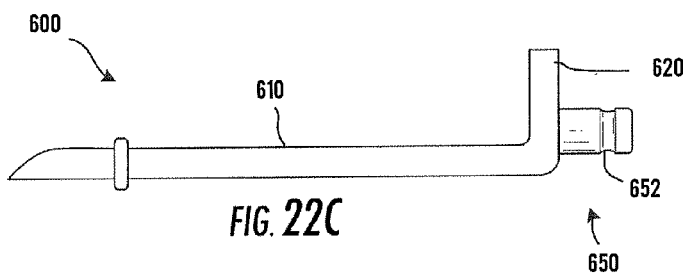

FIG. 22C illustrates yet another embodiment of blade 600 where a protrusion 650 extends from a distal face of abutment 620. The protrusion 650 may further include a groove 652. A corresponding engagement feature of a blade removal tool may be positioned over protrusion 650 and may engage with the groove 652 to facilitate removal of the blade 600.

Figure 22D:
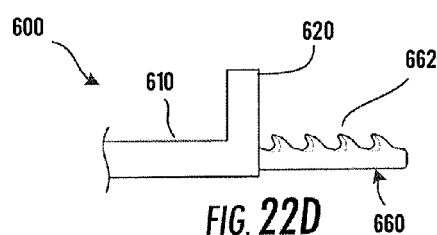

FIG. 22D illustrates yet another embodiment of blade 600 where a protrusion 660 extends from a distal face of abutment 620. The protrusion 660 includes teeth/gears 662 for engaging with a corresponding engagement feature of a blade removal tool.

Figure 23:
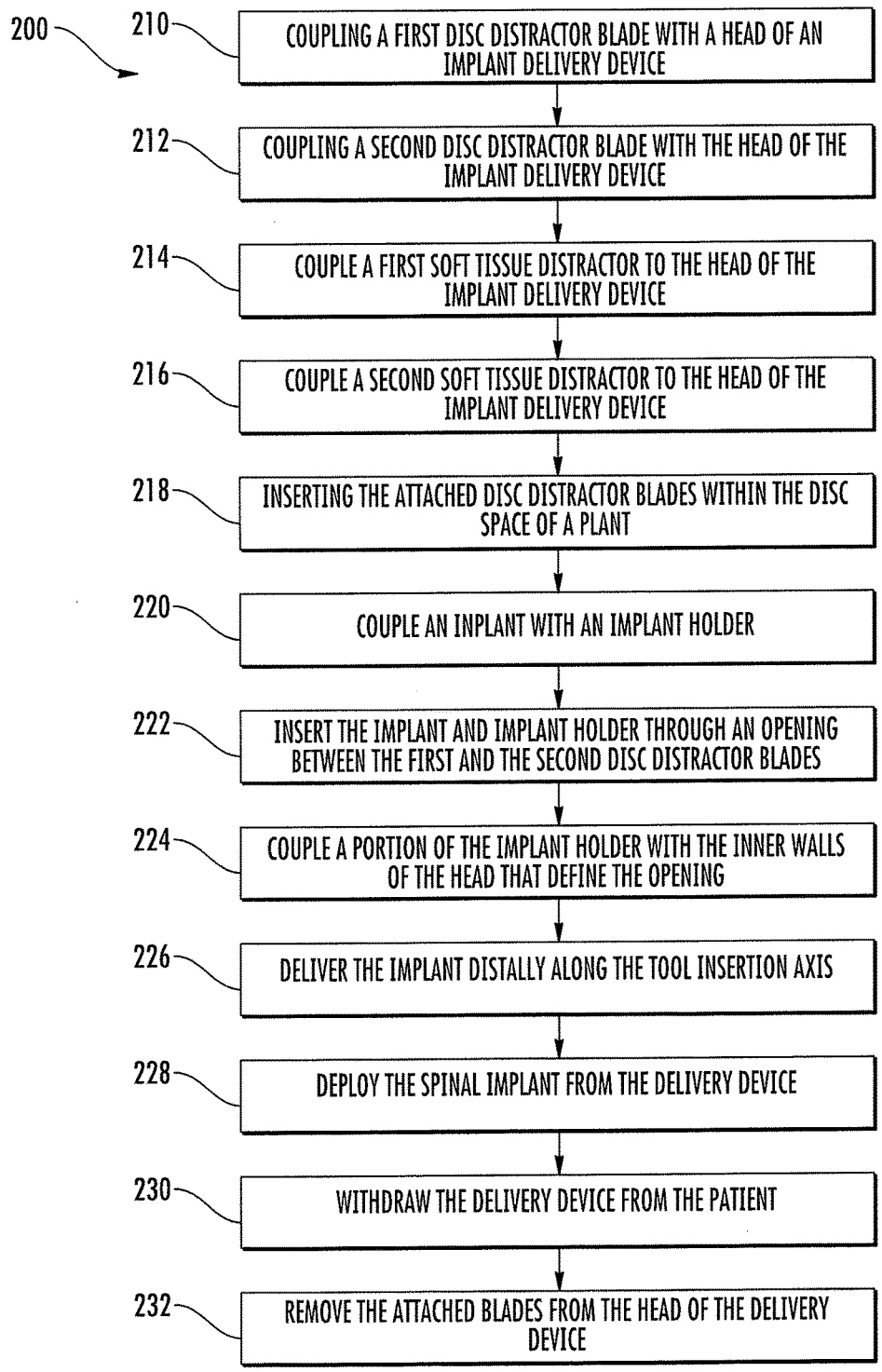
FIG. 23 is an exemplary method according to some embodiments of the present invention.

FIG. 23 illustrates an exemplary method 200 of implanting a spinal implant using embodiments of a device described above. Method 200 may start with coupling a first disc distractor blade with a head of an implant delivery device 210 and coupling a second disc distractor blade with the head of the implant delivery device 212. As mentioned above, the first disc distractor may be positioned opposite the second disc distractor and on opposite sides of an opening in the head. Optionally, a first soft tissue distractor may be coupled to the head of the implant delivery device 214 and a second soft tissue distractor may be coupled to the head of the implant delivery device 216. After steps 210-216, a delivery device may resemble, for example, the device 10 illustrated in FIG. 2 or the device 100 illustrated in FIG. 16. The method 200 may further include inserting the distal end of the disc distractor blades within the disc space of a patient 218. An implant may be coupled with an implant holder 220 prior to or after inserting the distal tips of the disc distractor blades within the disc space 218. The implant and implant holder assembly may then be inserted distally through an opening between the first and the second disc distractor blades 222. Optionally, a portion of the implant holder may be coupled with the inner walls of the head that define the opening 224 to help guide the implant and implant holder assembly along the tool insertion axis. The implant may be delivered distally along the tool insertion axis 226 and deployed from the delivery device to a deployment site 228. Thereafter, the delivery device may be withdrawn from the patient 230. The attached blades may then be removed from the head of the delivery device 232 for disposal or for sterilization and reuse.

The foregoing is provided for purposes of illustrating, explaining, and describing embodiments of the present invention. Further modifications and adaptations to these embodiments will be apparent to those skilled in the art and may be made without departing from the scope or spirit of the invention. Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:
1. A spinal implant delivery device comprising:
a handle;
a head supported by the handle, the head comprising an opening for receiving a tool there through and defining a tool insertion axis, the head further comprising a first pair of engagement features positioned on opposite sides of the opening, the first pair of engagement features configured to couple with one or more removable blades; and a first pair of removable blades configured to couple with the first pair of engagement features of the head and to extend distally from the head and taper toward each other from a proximal end of each of the first pair of removable blades to a distal end of each of the first pair of removable blades, each of the first pair of removable blades comprising a proximal engagement feature on the proximal end of each of the first pair of removable blades that is configured to engage with a removal tool;

wherein the opening of the head is defined by an inner wall, and wherein the inner wall is keyed to slideably and fittingly engage a body of a received implant holder to restrict translational movement of the implant holder to movement along the tool insertion axis so that the inner walls guide the implant holder as the implant holder slides along the tool insertion axis to deliver a spinal implant.

2. The device of claim 1, wherein the first pair of engagement features comprises at least one of slot apertures configured to receive a removable blade and dovetail engagement features configured to receive a body of the removable blade.

3. The device of claim 1, wherein the head further comprises a second pair of engagement features positioned on opposite sides of the opening, the second pair of engagement features configured to couple with one or more removable blades, whereby the first pair of engagement features and the second pair of engagement features permit removable attachment of four removable blades.

4. The device of claim 3, further comprising a second pair of removable blades, the second pair of removable blades configured to couple with the second pair of engagement features of the head, and wherein the first pair of removable blades and the second pair of removable blades form a rectangular channel for receiving and delivering a spinal implant.

5. The device of claim 1, wherein the handle has an elongate length defining a handle axis, and wherein the handle axis traverses the tool insertion axis.

6. The device of claim 1, further comprising an implant holder having a body with a rectangular cross-section, and wherein the inner wall of the opening defines a rectangular opening corresponding to the rectangular cross-section of the implant holder body.

7. The device of claim 1, wherein the inner walls of the opening are threaded to couple with threads on a received implant holder.

8. The device of claim 7, further comprising an implant holder having a body with a circular cross-section, wherein the inner wall of the opening defines a circular opening corresponding to the circular cross-section of the implant holder body, and wherein the threads of the opening cooperate with the threads of the implant holder to couple a rotational motion of the implant holder about the tool insertion axis with a translational motion of the implant holder along the tool insertion axis.

9. The device of claim 1, further comprising an implant holder having a body with distance indicia along a length of the implant holder, and wherein the implant holder cooperates with the head to identify a distance indicia corresponding to a position of the implant holder along the tool insertion axis relative to the head.

10. A spinal implant delivery device comprising:
a handle;
a head supported by the handle, the head comprising an opening for receiving a tool there through and defining a tool insertion axis, the head further comprising a first pair of engagement features positioned on opposite sides of the opening, the first pair of engagement features configured to couple with one or more removable blades; and
wherein the head further comprises a second pair of engagement features positioned on opposite sides of the opening, the second pair of engagement features configured to couple with one or more removable blades, whereby the first pair of engagement features and the second pair of engagement features permit removable attachment of four removable blades;
a first pair of removable disc distractors for maintaining proper distraction within a disc space;
a second pair of removable soft tissue distractors;
the first pair of removable disc distractors configured to couple with the first pair of engagement features of the head and to extend distally from the head and taper toward each other from a proximal end of each of the first pair of removable blades to a distal end of each of the first pair of removable blades;
the second pair of soft tissue distractors configured to couple with the second pair of engagement features of the head; and
wherein the first pair of disc distractors and the second pair of soft tissue distractors form a rectangular channel for receiving and delivering a spinal implant;
wherein the opening of the head is defined by an inner wall, and wherein the inner wall is keyed to slideably and fittingly engage a body of a received implant holder to restrict translational movement of the implant holder to movement along the tool insertion axis so that the inner walls guide the implant holder as the implant holder slides along the tool insertion axis to deliver a spinal implant.

11. The device of claim 5, wherein the handle axis and the tool insertion axis are at an angle between 90-110°.

12. The device of claim 11, wherein the handle axis and the tool insertion axis are perpendicular to one another.

13. The device of claim 10, wherein the disc distractors comprise a blade body and a blade abutment that projects from the blade body, the blade abutment cooperating with the first pair of engagement features to retain the disc distractors in a desired position relative to the head, and wherein the soft tissue distractors comprise a blade body and a blade abutment that projects from the blade body, the blade abutment cooperating with the second pair of engagement features to retain the soft tissue distractors in a desired position relative to the head.

14. The device of claim 10, wherein the disc distractors comprise a metal material and wherein the soft tissue distractors comprise a polymer material.

15. The device of claim 10, wherein the disc distractors comprise a stop at a distal end to prevent the disc distractors from being inserted too far into the disc space and wherein the soft tissue distractors do not comprise a stop.

16. A method for inserting a spinal implant to a deployment site within a patient by using a spinal implant delivery device having a handle and a head with an opening supported by the handle, the method comprising:
coupling a first disc distractor blade with a first engagement feature of the head of the spinal implant delivery device;

coupling a second disc distractor blade with a second engagement feature of the head of the spinal implant delivery device, the second engagement feature on an opposite side of the opening from the first engagement feature;
coupling a first soft tissue distractor to the head of the spinal implant delivery device;
coupling a second soft tissue distractor to the head of the spinal implant delivery device, the first and second disc distractor blades and the first and second soft tissue distractor blades defining a rectangular channel for receiving and deploying the spinal implant;
delivering the spinal implant through the opening of the head of the spinal implant delivery device;
deploying the spinal implant from the spinal implant delivery device;
withdrawing the spinal implant delivery device from within patient;
removing the first disc distractor blade and the second disc distractor blade from the head of the spinal implant delivery device; and
removing the first and second soft tissue distractors from the head of the spinal implant delivery device after deploying the spinal implant and withdrawing the spinal implant delivery device from within the patient.

17. The method of claim 16, further comprising:
coupling the spinal implant with a distal end of an implant holder;
manipulating a proximal end of the implant holder to translate the spinal implant distally along a spinal implant insertion axis defined by the opening of the head of the spinal implant delivery device; and
separating a distal end of the first distractor blade and a distal end of the second distractor blade by translating the spinal implant adjacent the distal ends of the first and second distractor blades.

18. The method of claim 17, wherein the opening of the head is defined by an inner wall, and wherein the method further comprises:
sliding the implant holder through the opening of the head of the spinal implant delivery device;
engaging a portion of the implant holder with inner wall such that translational movement of the implant holder is restricted to translational movement along the spinal implant insertion axis.

19. The method of claim 18, wherein a portion of the implant holder comprises threads and wherein the inner wall comprises corresponding threads, and wherein the method further comprises: threading the threads of the implant holder with the threads of the inner wall.

* * * * *